United States Patent [19]

Motzkau

[11] Patent Number: Plant 6,413

[45] Date of Patent: Nov. 22, 1988

[54] AZALEA PLANT NAMED ARDENT

[75] Inventor: Henry W. Motzkau, Lacey, Wash.

[73] Assignee: Yoder Brothers, Inc., Barberton, Ohio

[21] Appl. No.: 19,306

[22] Filed: Feb. 26, 1987

[51] Int. Cl.[4] ..... A01H 5/00

[52] U.S. Cl. ..... Plt./56

[58] Field of Search ..... Plt./55–57

*Primary Examiner*—James R. Feyrer

*Attorney, Agent, or Firm*—Schwartz, Jeffery, Schwaab, Mack, Blumenthal & Evans

[57] ABSTRACT

An Azalea plant named Ardent, particularly characterized by its shiny evergreen foliage, long lasting flowers, hot pink flower color, single hose-in-hose flower form, resistance to foliage burn and spider mite infestation, ease of budding in a year round controlled program, and excellent shipping, and cooler tolerance.

1 Drawing Sheet

The present invention comprises a new and distinct cultivar of Azalea plant named Ardent obtained from crossing certain Azalea selections in a program of controlled hybridization by applicant in Lacey, Wash. The seed parent in the breeding program was identified by Code #2233, and the pollen parent by Code #1040.

The new cultivar is similar in many respects to the cultivar Solitaire, disclosed in U.S. Plant Pat. No. 3,171, having the same characteristics as Solitaire of:

1. Similar flowering time.
2. Evergreen foliage.
3. Branches somewhat brittle.
4. Long lasting flowers.
5. Ease of budding.

The new cultivar is distinguished from Solitaire by the following characteristics:

1. Smaller, darker and shiny green leaves.
2. No dominant spreading shoots.
3. Flower color is a hotter or more vivid and deeper pink.
4. More resistant to foliage burn and spider mite infestation.

The new cultivar was selected by applicant in Lacey, Wash. from the seedling progeny of the above mentioned parents. Varietal worth was determined by flowering liners from cuttings taken from the initial selection in both a year round and natural season developmental flowering program over a period of 3½ years. Stock growth was evaluated in the vicinity of Southern Florida.

The new cultivar was first asexually reproduced by applicant in Lacey, Wash. by cuttings, and subsequent propagation has taken place at Fort Myers, Fla. Ardent has been found to retain its distinctive characteristics through successive propagations.

When grown in the vicinity of Fort Myers, Fla., Ardent has a response described as early to mid-season, and the following detailed description is based on observations made of the new cultivar from field grown plants in Fort Myers, Fla. The response time and blooming period may vary significantly with varying environmental conditions such as temperature and amount of daylight. Suggested flowering period is from December 15 through April in a natural season program and all year in a year round controlled program.

The accompanying photograph shows in perspective view the unique features of the new cultivar, with colors being as true as possible with color illustrations of this type. Color references are to The Royal Horticultural Society Colour Chart. Where a particular color value is not precise, variations from the closest color value have been noted.

Botanical classification: *Rhododendron hybrida,* evergreen type.

Flower:

*Color.*—Reading location and season: All color readings were taken in an office having cool white florescent fixtures and facing a west window. All readings were taken in October in Fort Myers, Fla. between the hours of 10:00 a.m. and 2:00 p.m. General tonality: Hot pink 68A. Sepals first divide: Darker than dark hot pink 63B. Petals unfurl: Darker than dark hot pink 67C. Fully open: Hot pink 68A. Inside of petals: Hot pink 68A. Reverse of petals: Hot pink 73D. Base of petals: Light pink 62D. Outer hose: Hot pink 68A. Base of outer hose: Light pink 62D. Variations (dotted): Appear on 3 petals per whorl (hose); color, purple red 57B.

*Buds.*—Size: Medium. Form: Conoidal. Opening habit: From a rose-bud shape to a cupped form.

*Bloom.*—Size: Medium, average 7 cm, range 6.5–8.0 cm. Borne: Several together, average 3, range 1–3. Form: Majority of flowers are single hose-in-hose, yet some have a number of petaloid centers and are semi-double hose-in-hose.

*Blooming habit.*—Once, profusely. Response: Natural season: Early to mid-season. Year round: All twelve months.

*Calyx.*—Normal.

*Peduncle.*—Length: 3 cm. Aspect: Hairy. Strength: Flexible, semi-strong.

*Petals.*—Texture: Soft. Substance: Heavy. Appearance: Inside: Satiny. Outside: Satiny. Form: Obovate, edge entire, irregularly undulate. Arrangement: Imbricate. Fragrance: None. Persistance: Non shatter. Longevity (keeping quality): Greenhouse: 3 weeks. Home: 4 weeks.

Reproductive organs:

*Stamen-anthers.*—Variable in number, most flowers having no stamens; when present, anthers are fused to petaloid filaments. Immature: Purple red 57B. Mature: Brownish grey 175A–175B.

*Filaments.*—Rarely present in columnar form, most are petaloid. Color, light pink 62B.

*Style.*—Normal, columnar; curved upon maturity, lavender pink 58D.

*Stigma.*—Normal, discoid. Immature: Green 141C. Mature: Orange brown 165B.

*Ovaries.*—Normal, hairy.

Fruit: None.

Foliage:

*Type.*—Evergreen.

*Leaflets.*—Single.

*Size.*—Length: Average, 5 cm, range 4.75–5.25 cm. Width: Average, 2.5 cm, range 2–3 cm. Shape: Oblong. Texture: Upper glossy; lower somewhat glossy, hairy. Rib and mid veins: Slightly depressed. Edge: Very shallowly crenate.

*Color (immature foliage).*—Upper surface: Dark green 135A. Lower surface: Dark green 137B.

*Color (mature foliage).*—Upper surface: Darker than dàrk green 136A. Lower surface: Dark green 137B.

*Petiole.*—Short, slightly hairy, light green.

Plant (bush):

*Growth habit.*—Semi-upright.

*Breaking habit.*—Good.

*Rooting habit.*—Good.

*Budding ease.*—Good.

*Uniformity of budding.*—Good; has some dominant shoots that are slow to bud.

*Growth regulator.*—Small amounts at certain times.

*Stems (color).*—Immature wood: Darker than light green 144B. Mature wood: Dark brown 165A.

*Responsiveness to day length and temperature.*—Buds easily and uniformly over a wide range of environmental conditions.

*Resistance to cylindrocladium.*—Good.

*Cooler tolerance.*—Excellent.

*Shipping tolerance.*—Excellent.

I claim:

1. A new and distinct cultivar of Azalea named Ardent, as described and illustrated, and characterized particularly as to novelty by its evergreen foliage, long lasting flowers, hot pink flower color, single hose-in-hose flower form, shiny foliage, resistance to foliage burn and spider mite infestation, ease of budding in a year round controlled program, excellent shipping, and cooler tolerance.

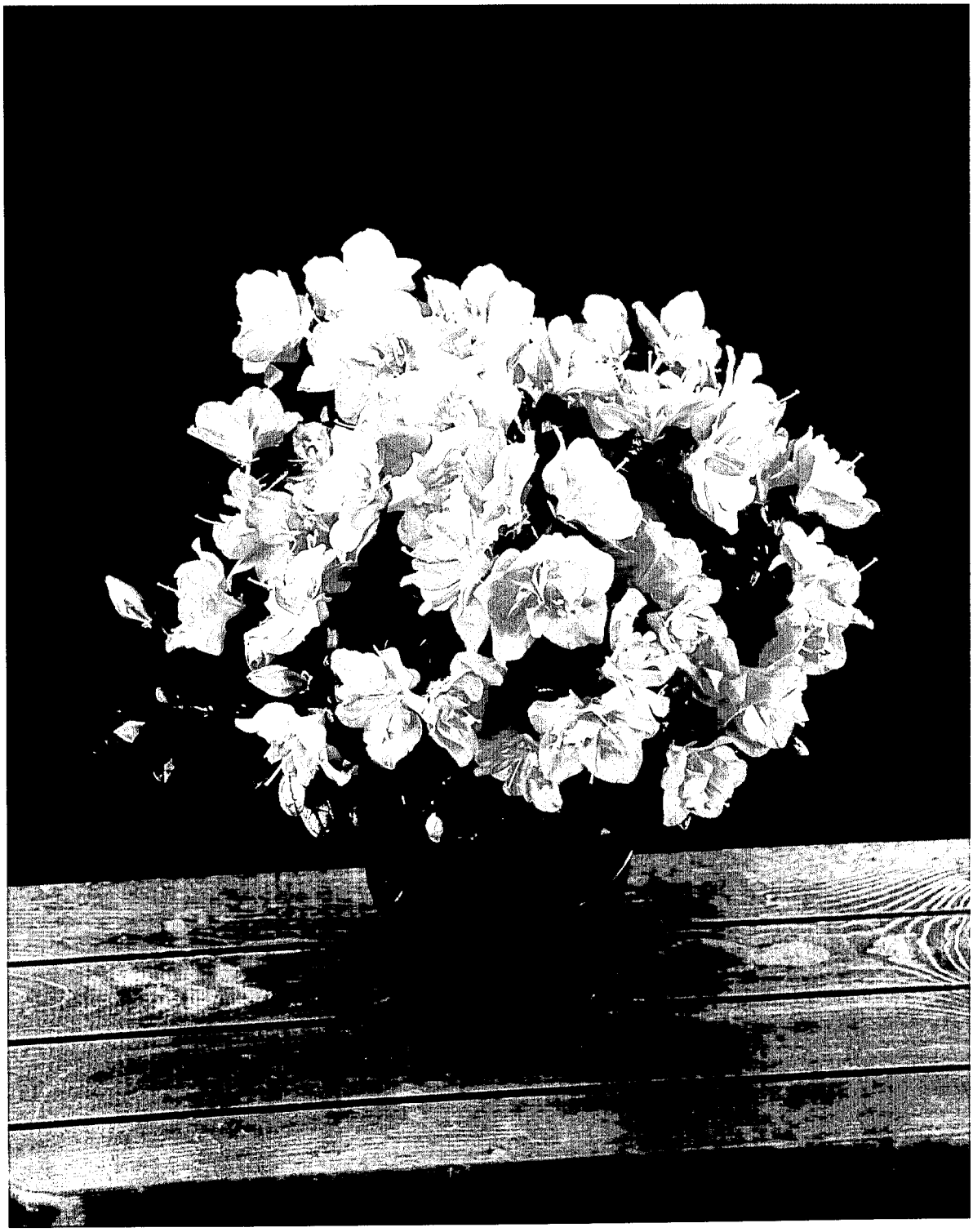

* * * * *